United States Patent
Sargent, Jr.

(10) Patent No.: US 8,425,466 B2
(45) Date of Patent: Apr. 23, 2013

(54) HINGED CATHETER

(75) Inventor: Peter William Sargent, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 377 days.

(21) Appl. No.: 12/908,398

(22) Filed: Oct. 20, 2010

(65) Prior Publication Data

US 2012/0101441 A1   Apr. 26, 2012

(51) Int. Cl.
*A61M 5/178* (2006.01)

(52) U.S. Cl.
USPC .............. 604/164.13; 604/164.03; 604/95.04; 604/264; 604/523; 604/528; 604/532

(58) Field of Classification Search ............. 604/164.13, 604/95.04, 164.03, 528, 532, 264, 523
See application file for complete search history.

(56) References Cited

U.S. PATENT DOCUMENTS

| | | | |
|---|---|---|---|
| 5,489,269 A | | 2/1996 | Aldrich et al. |
| 5,730,724 A | | 3/1998 | Plishka et al. |
| 6,508,789 B1 | * | 1/2003 | Sinnott et al. ............ 604/164.02 |

FOREIGN PATENT DOCUMENTS

| WO | WO 02/30310 A1 | 4/2002 |
|---|---|---|
| WO | WO 2009/089038 A1 | 7/2009 |

OTHER PUBLICATIONS

International Search Report for International Application No. PCT/US2011/055896, dated Feb. 13, 2012, 2 pages.
Written Opinion of the International Searching Authority for International Application No. PCT/US2011/055896, dated Feb. 13, 2012, 6 pages.

* cited by examiner

*Primary Examiner* — Kevin C Sirmons
*Assistant Examiner* — Edelmira Bosques
(74) *Attorney, Agent, or Firm* — Brinks Hofer Gilson & Lione

(57) ABSTRACT

The disclosure provides a catheter for positioning in a contralateral femoral approach in highly angulated iliac bifurcations. The catheter comprises an elongate shaft, an adjustable element, and a wire entrance port on the elongate shaft. The elongate shaft has a proximal portion, an intermediate portion, a curved portion, and a distal portion. The curved portion connects the intermediate portion and the distal portion. The adjustable element is configured to encompass the distal portion and the intermediate portion together in a closed position. The adjustable element can be removed away from the distal portion permitting the distal portion in an open position. The wire entrance port is disposed in the intermediate portion near the curved portion. The distal portion is biased to be spaced away from the intermediate portion in the open position. The adjustable element is connected to an operating wire configured to advance and retreat through the wire entrance port.

17 Claims, 4 Drawing Sheets

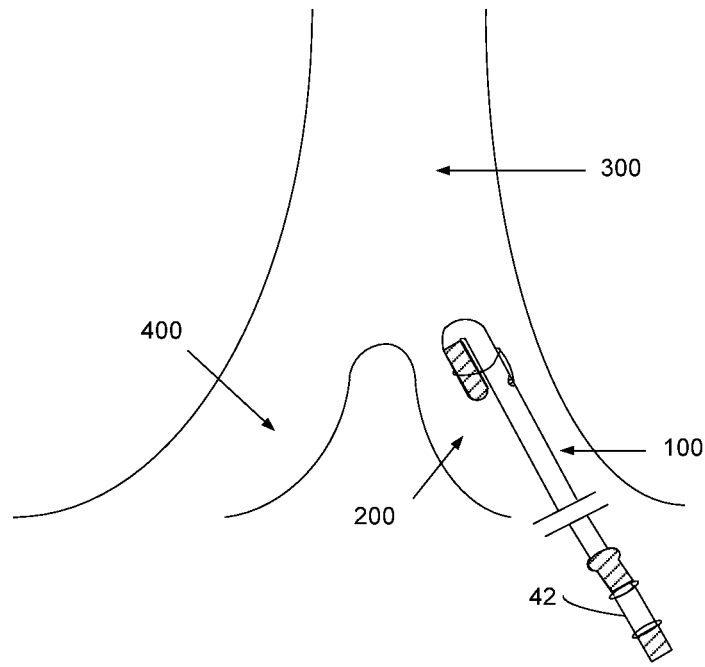
FIG. 3 (step 1)
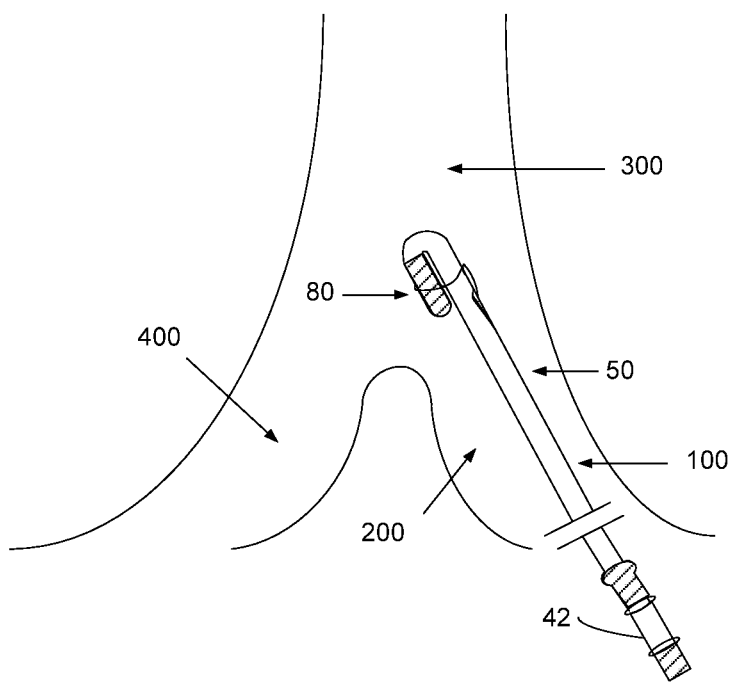
FIG. 4 (step 2)

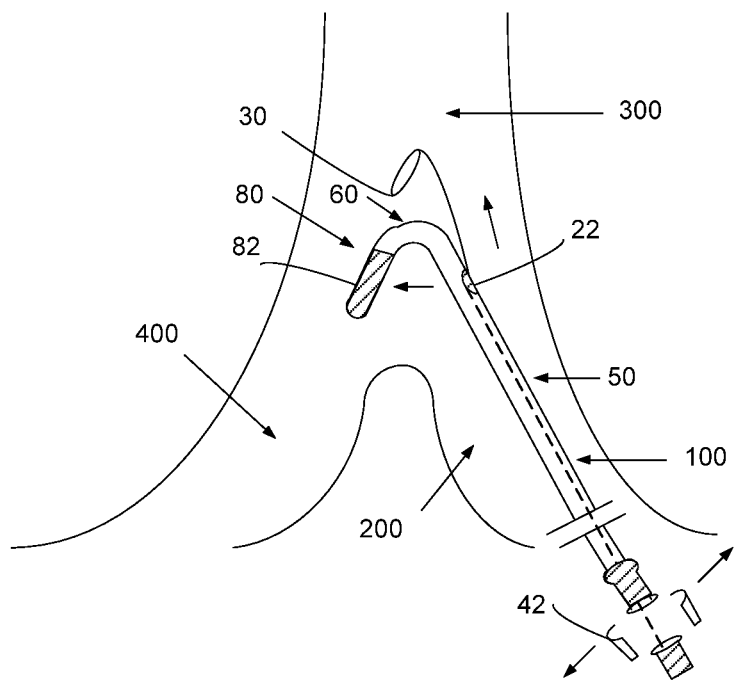
FIG. 5 (step 3)
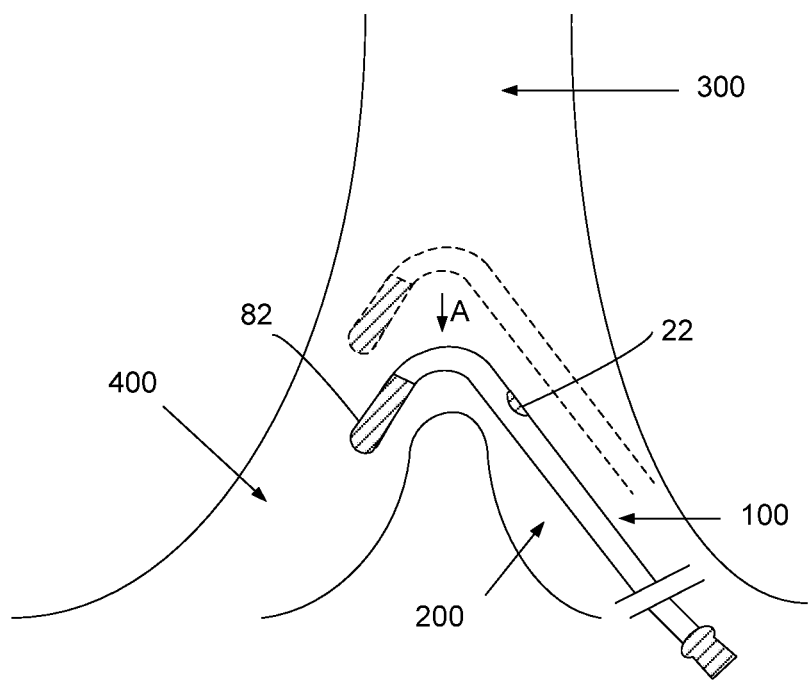
FIG. 6 (step 4)

HINGED CATHETER

BACKGROUND

The present disclosure relates generally to a hinged catheter for positioning in a contralateral femoral approach in highly angulated iliac bifurcations for medical intervention.

Interventional cardiologists, interventional radiologists, and vascular surgeons use catheters as a minimally invasive device in interventional procedures such as angioplasty and stenting. In the interventional procedures, the catheters need to be positioned in highly angulated iliac bifurcations. In angioplasty, the catheter is used to mechanically widen a narrowed or obstructed blood vessel. In stenting, the stent stays in the artery permanently to hold the artery open.

Wires or sheathes are currently used to gain access "up and over" the iliac bifurcation. For example, the Flexor® Check-Flo® Introducer Set by COOK Medical Incorporated can be used to introduce balloon, diagnostic and guiding catheters or other devices. Current technologies, however, make gaining access in highly angulated bifurcations difficult and dangerous. Because the contralateral femoral approaches in highly angulated iliac bifurcations are difficult to gain access by traditional wires or sheaths, it is desirable to have a device to quickly and safely position the catheters in highly angulated iliac bifurcations.

SUMMARY

The present invention provides a hinged catheter for positioning in a contralateral femoral approach in highly angulated iliac bifurcations.

One embodiment of the hinged catheter comprises an elongate shaft, an adjustable element, and a wire entrance port on the elongate shaft. The elongate shaft has a proximal portion, an intermediate portion, a curved portion, and a distal portion. The curved portion connects the intermediate portion and the distal portion. The distal portion has a distal end. The adjustable element is configured to encompass the distal portion and the intermediate portion together in a closed position. The adjustable element can be removed or spaced away from the distal portion to permit the distal portion to move into an open position. The wire entrance port is disposed in the intermediate portion near the curved portion. The distal portion is biased to be spaced away from the intermediate portion in the open position. The adjustable element is connected to an operating wire that is configured for advancing and retreating through the wire entrance port.

In another aspect of the present invention, there is provided a method for using a catheter. The method comprises: providing the catheter having: (i) an elongate shaft having a proximal portion, an intermediate portion, a curved portion, and a distal portion, the curved portion connecting the intermediate portion and the distal portion, the distal portion having a distal end; (ii) an adjustable element configured to encompass the distal portion and the intermediate portion together in a closed position, the adjustable element removable away from the distal portion to permit the distal portion to move into an open position; and (iii) a wire entrance port disposed in the intermediate portion near the curved portion; advancing the catheter in the closed position through a bifurcation from femoral approach; and past the bifurcation into an aorta; advancing the operating wire to the support manifold; pushing the adjustable element past the curved portion of the catheter; and releasing the distal portion of the catheter shaft into the open position.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

FIG. 3 is an illustration of step 1 in the method of using a catheter of FIG. 1.

FIG. 4 is an illustration of step 2 in the method of using a catheter of FIG. 1.

FIG. 5 is an illustration of step 3 in the method of using a catheter of FIG. 1.

FIG. 6 is an illustration of step 4 in the method of using a catheter of FIG. 1.

DETAILED DESCRIPTION OF THE PREFERRED EMBODIMENTS

In the present application, the term "proximal" refers to a direction that is generally toward a physician during a medical procedure, while the term "distal" refers to a direction that is generally toward a target site within a patient's anatomy during a medical procedure.

Figure 1:
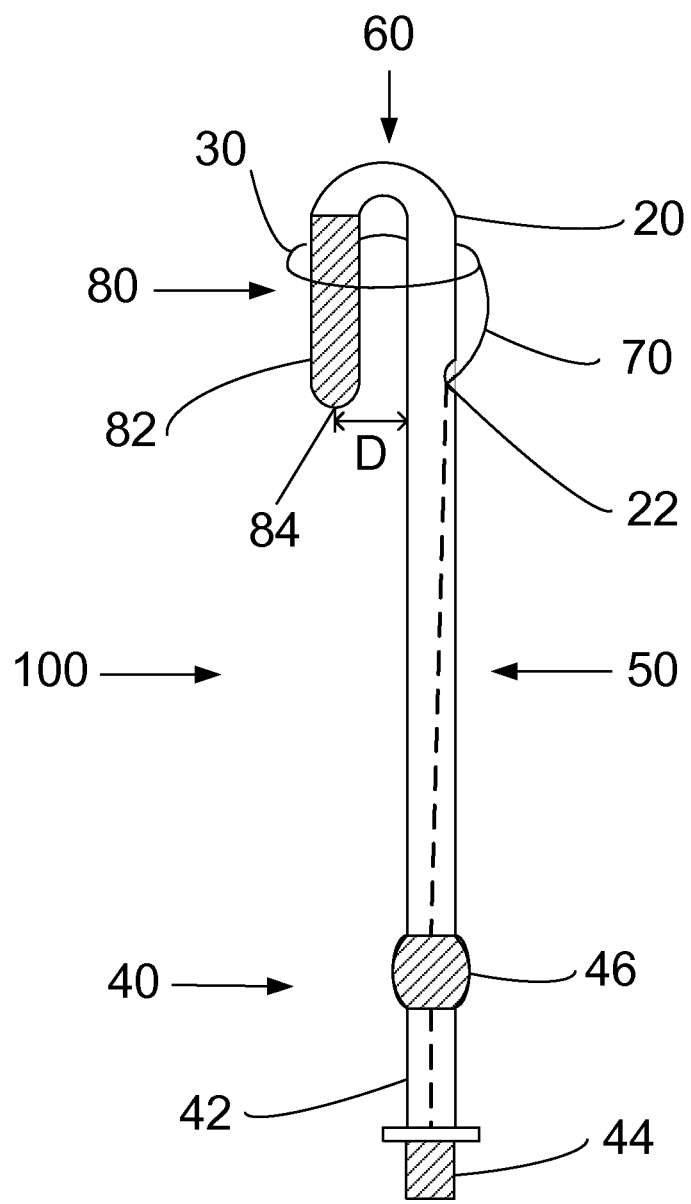
FIG. 1 is an illustration of an embodiment of the hinged catheter.

Referring now to FIG. 1, a first embodiment of the hinged catheter 100 is disclosed. The hinged catheter 100 comprises an elongate shaft 20, an adjustable element 30, and a wire entrance port 22 on the elongate shaft 20. The elongate shaft 20 has a proximal portion 40, an intermediate portion 50, a curved portion 60, and a distal portion 80. The curved portion 60 connects the intermediate portion 50 and the distal portion 80. The distal portion 80 has a distal end 84. The adjustable element 30 is configured to encompass and hold the distal portion 80 and the intermediate portion 50 together in a closed position. The adjustable element 30 can be removed away from the distal portion 80 thereby permitting the distal portion 80 to move into an open position. The wire entrance port 22 is disposed in the intermediate portion 50 near the curved portion 60. The wire entrance port 22 may be created by either skiving or puncturing to create a port for the operating wire 70 to advance and retreat. The distal portion 80 is biased to be spaced away from the intermediate portion 50 in the open position. The adjustable element 30 is connected to an operating wire 70 that is configured to be advanced and retreated through the wire entrance port 22.

The hinged catheter 100 may further comprise a peel away sheath 42 near the proximal end of the elongate shaft 20. The peel away sheath 42 provides support when advancing the elongate shaft 20 in the closed position as shown in FIGS. 3-4 and prevents inadvertent advancement of the operating wire 70 relative to the elongate shaft 20. Once the catheter is in position, the peel away sheath 42 is removed to permit advancement of the operating wire 70. The distal portion 80 of the hinged catheter 100 may further comprise a radiopaque portion 82.

The elongate shaft 20 may be made of a nylon, Polyimide, Teflon, Polypropylene, and Silicone. The operating wire 70 is made of a sufficiently flexible metal with appropriate stiffness. Specifically, the operating wire 70 may be made of varying alloys. For example, the operating wire 70 may be made of at least one of the following material: nitinol and stainless steel. The operating wire 70 may further comprise a proximal hub 44 configured for advancing, rotating, and retracting the operating wire 70.

Figure 2A:
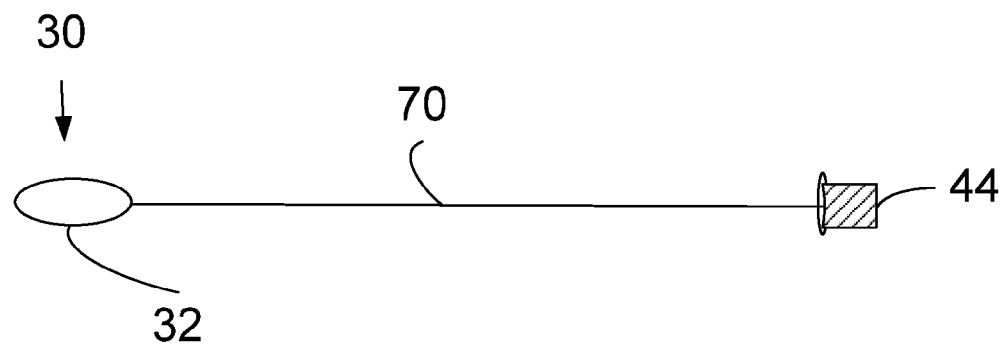
FIG. 2A is an illustration of the adjustable element of the hinged catheter.

As shown in FIG. 2A, the adjustable element 30 comprises a hoop 32. The hoop 32 may be manipulated to adjust the position of the distal portion 80 by adjusting the shape of the hoop 32 or by pulling distantly the operating wire 70. For example, the shape of the hoop 32 may be changed from circular to an ellipse or other shape. The hoop 32 may also be controlled by manipulating the hoop securement wire proximal hub 44. The joint angle between the hoop 32 and the operating wire 70 may be adjusted differently in the open and closed positions. The stiffness of the hoop 32 is less than the stiffness of the operating wire 70. The operating wire 70 needs to be sufficiently stiff to be push the hoop 32 off the hinged distal portion 80 without excessive bowing. The hoop 32 needs to be flexible enough to collapse into the catheter shaft 20 during removal. In a closed position shown in FIGS. 1 and 4, the distal portion 80 is adjusted to be positioned close to or adjacent to the intermediate portion 50. The distal portion 80 of the elongate shaft 20 is bent larger than 150 degrees in a closed position. More preferably, the distal portion 80 of the elongate shaft 20 is bent larger than 170 degrees in the closed position. The distance D between the distal end 84 and the intermediate portion 50 is substantially zero in the closed position.

Figure 2B:
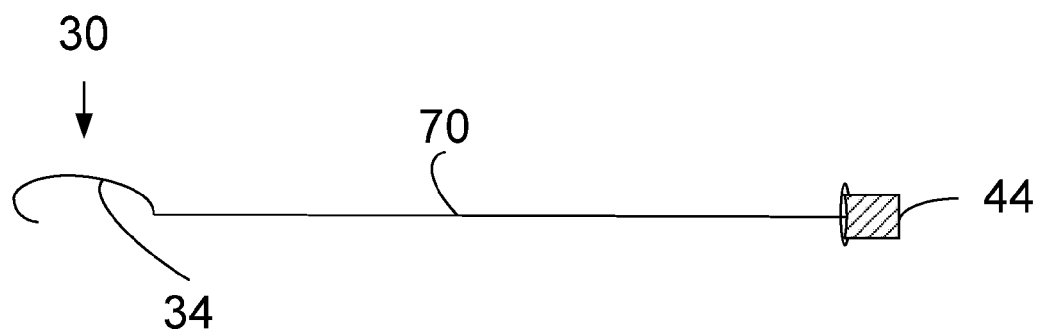
FIG. 2B is another illustration of the adjustable element of the hinged catheter.

Similarly, in FIG. 2B, the adjustable element 30 comprises a hook 34. The hook 34 may be manipulated to adjust the position of the distal potion 80. The hook 34 may be controlled by manipulating the hoop securement wire proximal hub 44. The distal portion 80 is biased to be spaced away from the intermediate portion 50 in an open position as in FIG. 5. More specifically, the distal portion 80 of the elongate shaft 20 is in bent less than 150 degrees in the open position.

The hinged catheter 100 may be used in many applications to introduce catheters for minimally invasive surgeries or diagnoses. For example, in angioplasty, the elongate medical device to be introduced may be a balloon catheter. In other applications such as embolotherapy, the elongate medical device may be a non-tapered end catheter.

FIGS. 3-6 show an exemplary method for introducing and advancing a hinged catheter 100 to the aorta 300 through iliac branches. In FIG. 3, the hinged catheter 100 is in a closed position and disposed in the iliac branch 200. In this step, a hinged catheter 100 is positioned in the aorta 300. The hinged catheter 100 has (i) an elongate shaft 20 having a proximal portion 40, an intermediate portion 50, a curved portion 60, and a distal portion 80, the curved portion 60 connecting the intermediate portion 50 and the distal portion 80, the distal portion 80 having a distal end 84; (ii) an adjustable element 30 configured to encompass and hold the distal portion 80 and the intermediate portion 50 together in a closed position, the adjustable element 30 can be removed away from the distal portion 80 thereby permitting the distal portion 80 to move into an open position; and (iii) a wire entrance port 22 disposed in the intermediate portion 50 near the curved portion 60.

In FIG. 4, the hinged catheter 100 is in a closed position positioned in the aorta 300. The hinged catheter 100 is advanced through the bifurcation from femoral approach. An operator may advance the hinged catheter 100 in the closed position past the bifurcation into an aorta 300. The operator may observe the position of the distal end 80 on a medical imaging device such as an ultrasound imaging device, an X-ray imaging device, or any other compatible medical imaging devices.

In FIG. 5, after advancing the operating wire to the support manifold, the operator pushes the adjustable element 30 past the curved portion 60 of the catheter 100 and releases the catheter shaft to the open position. FIG. 5 shows that the hinged catheter 100 is in an open position disposed in the aorta 300. The adjustable element 30 is manipulated to allow the distal portion 80 to be in a natural state. The peel away sheath 42 may also be removed to provide distance for advancement of the adjustable element 30. The hinged catheter 100 is advanced past the bifurcation into the aorta 300. The operating wire 70 is advanced to the support manifold, pushing the adjustable element 30 past the curved portion 60 of the hinged catheter 100. Thus, the catheter shaft 20 is in an open position with the distal portion 80 in a natural position spread away from the intermediate portion 50.

In FIG. 6, the adjustable element 30 and the operating wire 70 are removed though the wire entrance port 22 and pulled out of the body. The opened hinged catheter 100 would then be pulled along direction A so that the stiffness of the catheter would keep the opened distal portion 80 from pulling back down the access iliac 200. The opened distal portion 80 may be kept in open position by the material tension of the catheter itself. Additionally or alternatively, the opened distal portion 80 may be kept in open position using mechanical inserts or springs. The radiopaque open arm tip 82 may be used to verify entrance into the contralateral iliac 400. The hinged catheter 100 would then be held in position and a wire would be advanced through the catheter shaft 20 to gain access into the contralateral iliac 400 and the entire system removed over the newly placed wire.

The method may further comprise verifying entrance into the contralateral iliac by a radiopaque portion 82 of the distal portion 80. The hinged catheter 100 may further comprise at least one of the following: a hoop and a hook. The operator may use an ultrasound imaging device or other medical imaging devices to monitor the whole procedure.

Alternatively or additionally, the operator may use a computer to manipulate the hinged catheter 100 and/or the adjustable element 30 according to a program stored in a computer-readable storage medium, such as Read-Only Memory (ROM), Random Access Memory (RAM), magnetic disc and compact disc.

While various embodiments of the invention have been described, it will be apparent to those of ordinary skill in the art that many more embodiments and implementations are possible within the scope of the invention. The different aspects of the described embodiments may be combined together to improve the performance of the hemodialysis catheter. Accordingly, the invention is not to be restricted except in light of the attached claims and their equivalents. Moreover, the advantages described herein are not necessarily the only advantages of the invention and it is not necessarily expected that every embodiment of the invention will achieve all of the advantaged described.

What is claimed is:

1. A hinged catheter for positioning in a contralateral femoral approach in highly angulated iliac bifurcations, the hinged catheter comprising:

an elongate shaft having a proximal portion, an intermediate portion, a curved portion, and a distal portion, the curved portion connecting the intermediate portion and the distal portion, the distal portion having a distal end;

an adjustable element configured to encompass the distal portion and the intermediate portion together in a closed position, the adjustable element can be removed away from the distal portion permitting the distal portion in an open position; and a wire entrance port disposed in the intermediate portion near the curved portion;

wherein the distal portion is biased to be spaced away from the intermediate portion in the open position, and wherein the adjustable element is connected to an operating wire that is configured to advancing and retreating through the wire entrance port.

2. The hinged catheter of claim 1 further comprising a peel away sheath near the proximal end of the elongate shaft.

3. The hinged catheter of claim 2, wherein the peel away sheath provides support when advancing the elongate shaft in the closed position.

4. The hinged catheter of claim 2, wherein the peel away sheath is removed to provide distance for advancing the operating wire.

5. The hinged catheter of claim 1, wherein the distal portion comprises a radiopaque portion.

6. The hinged catheter of claim 1, wherein the distal portion of the elongate shaft is bent larger than 150 degrees in the closed position.

7. The hinged catheter of claim 1, wherein the distal portion of the elongate shaft is in bent less than 150 degrees in an open position.

8. The hinged catheter of claim 1, wherein the elongate shaft is made of at least one of nylon, Polyimide, Teflon, Polypropylene, and Silicone.

9. The hinged catheter of claim 1, wherein the operating wire is made of at least one of nitinol and stainless steel.

10. The hinged catheter of claim 1 further comprising a proximal hub configured for rotating, advancing, and retracting the operating wire.

11. The hinged catheter of claim 1, wherein the adjustable element comprises one of a hoop and a hook.

12. A method for using a catheter, the method comprising: providing the catheter having (i) an elongate shaft having a proximal portion, an intermediate portion, a curved portion, and a distal portion, the curved portion connecting the intermediate portion and the distal portion, the distal portion having a distal end; (ii) an adjustable element configured to encompass the distal portion and the intermediate portion together in a closed position, the adjustable element can be removed away from the distal portion permitting the distal portion in an open position; and (iii) a wire entrance port disposed in the intermediate portion near the curved portion, advancing the catheter in the closed position through a bifurcation from femoral approach; advancing the catheter in the closed position past the bifurcation into an aorta; pushing the adjustable element past the curved portion of the catheter; and releasing the catheter shaft to the open position.

13. The method of claim 12, further comprising removing the operating wire through the wire port.

14. The method of claim 12, further comprising verifying entrance into the contralateral iliac by a radiopaque portion of the distal portion.

15. The method of claim 12, wherein the hinged catheter further comprises a peel away sheath near the proximal end of the elongate shaft.

16. The method of claim 15, further comprising removing the peel away sheath.

17. The method of claim 12, wherein the hinged catheter further comprises at least one of the following: a hoop and a hook.

\* \* \* \* \*